(12) United States Patent
Davister et al.

(10) Patent No.: US 6,391,843 B1
(45) Date of Patent: *May 21, 2002

(54) CHEMICAL LINKER COMPOSITIONS

(75) Inventors: Michele Davister, Liege; Guy Broze, Grace-Hollogne; Patrick Durbut, Verviers; Hoai-Chau Cao, Liege, all of (BE); Thomas Connors, Piscataway, NJ (US); John Labows, Horsham, PA (US); Anne-Marie Misselyn, Villers l'eveque (BE)

(73) Assignee: Colgate-Palmolive Co., Piscataway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/653,686

(22) Filed: Sep. 1, 2000

Related U.S. Application Data

(63) Continuation-in-part of application No. 09/212,912, filed on Dec. 16, 1998, now Pat. No. 6,150,321, which is a continuation-in-part of application No. 08/764,342, filed on Dec. 12, 1996, now Pat. No. 5,854,194.

(51) Int. Cl.$^7$ .................. C11D 10/02; C11D 17/00; A01N 25/24

(52) U.S. Cl. ............ 510/426; 106/15.05; 424/59; 424/275.1; 424/405; 424/407; 510/101; 510/405; 510/421; 510/422; 510/423; 510/424; 510/425; 510/427; 510/535; 510/536; 510/537

(58) Field of Search .................. 106/15.05; 424/59, 424/275.1, 405, 407; 510/101, 405, 421, 422, 423, 424, 425, 426, 427, 535, 536, 537

(56) References Cited

U.S. PATENT DOCUMENTS

| | | | | |
|---|---|---|---|---|
| 5,854,194 A | * | 12/1998 | Davister et al. | 510/422 |
| 6,020,301 A | * | 2/2000 | Davister et al. | 510/417 |
| 6,150,321 A | * | 11/2000 | Davister et al. | 510/422 |
| 6,172,032 B1 | * | 1/2001 | Davister et al. | 510/417 |
| 6,197,732 B1 | * | 3/2001 | Davister et al. | 510/122 |
| 6,197,741 B1 | * | 3/2001 | Davister et al. | 510/417 |

* cited by examiner

Primary Examiner—Anthony Green
(74) Attorney, Agent, or Firm—Richard E. Nanfeldt

(57) ABSTRACT

A composition comprising: an organic chemical having a chemical group having a dipole moment of at least about 1.5 Debyes and a chemical linker selected from the group consisting of carboxylic acids having 4 to 6 carbon atoms, an ethoxylated polyhydric alcohol, a polyvinyl pyrrolidone and a polyethylene glycol having a molecular weight of about 600 to about 10,000, wherein the molar ratio of organic chemical to chemical linker is about 4:1 to 1:4.

3 Claims, No Drawings

CHEMICAL LINKER COMPOSITIONS

RELATED APPLICATION

This application is a continuation in part application of U.S. Ser. No. 9/212,912 filed Dec. 16, 1998, now U.S. Pat. No. 6,150,321, which in turn is a continuation in part application of U.S. Ser. No. 8/764,342 filed Dec. 12, 1996, now U.S. Pat. No. 5,854,194.

FIELD OF THE INVENTION

The present invention relates to a chemical linkers that can be added to an organic chemical such as a perfume, insect repellent, antibacterial agent, and/or an allergen agent in order to reduce the rate of vaporization of the chemical additive from the surface to which it has been applied.

BACKGROUND OF THE INVENTION

A major problem is how long a chemical additive such as a perfume, fabric softener, sunscreen agent, insect repellent, antibacterial agent and/or allergen agent will be effective on a surface on which the chemical has been deposited. For example, if the lasting effect of a perfume deposited on the human skin could be increased the necessity for repeat application of the perfume would be reduced. Alternatively, if the concentration of the perfume in a solution could be reduced while maintaining its effectiveness substantial cost savings could be achieved. The present invention relates to chemical linkers which can be added to the organic chemical whereby the chemical linker by chemical association links the organic chemical to the surface on which the organic chemical has been deposited thereby decreasing the rate of vaporization of the organic chemical. The requirement of the chemical linker is that when the chemical linker is added to a organic chemical that an exothermic interaction occurs between the chemical linker and the organic chemical which causes a reduction in the active vapor pressure of the organic chemical.

The instant invention further relates to the use of the chemical linkers and the organic chemical in a surfactant based cleaning compositions.

For example, Methylneodecanamide (MNDA) is an insect repellent agent which can be added to a hard surface cleaning composition. This is necessary to deposit 10 micrograms of MNDA per cm2 to have one day efficacy. It is more than 500 molecular layers. To deliver this amount requires almost neat usage and is not compatible with consumers habits and practice. Unfortunately, one may not increase the MNDA concentration. It is desirable to increase the repellency duration without increase MNDA quantity.

On the other hand, it would be desirable to have more formulation flexibility with high oil uptake capacity perfumes. The increase of the substantivity of these perfumes ingredients would make possible to either increase performance of the perfume, or deliver the same cleaning and olfacting results with less perfume. This invention teaches that chemical linkers are a way to deliver more efficiently actives such as MNDA or perfumes to a surface to which it has been applied.

SUMMARY OF THE INVENTION

The present invention relates to chemical compositions which comprise approximately by weight a complex of:

(a) an organic chemical having a chemical group with a dipole moment of at least about 1.5 selected from the group consisting of a chemical compound containing an amide linkage such as an insect repellents, antibacterial agents containing a carbon-halogen bond such as triclosan, allergen agents, fabric softener or sunscreen agent containing an ester group or enzymes containing acid groups and a chemical compound containing an aldehyde group or alcohol group such as those type of compounds present in perfumes and mixtures thereof; and (b) a chemical linker which undergoes an exothermic reaction with the organic chemical, wherein the chemical linker can be a polyvinyl pyrrolidone polymer, an ethoxylated polyhydric alcohol, carboxylic acid having about 4 to about 6 carbon atoms and a polyethylene glycol having a molecular weight of about 600 to about 10,000, preferably about 1,000 to about 8,000 wherein the mole ratio of the organic chemical to the chemical linker is about 4:1 to about 1:4.

The instant compositions excluded the use of ethoxylated nonionic surfactants formed for the condensation product of primary or secondary alkanols and ethylene oxide or propylene oxides because the use of these ethoxylated nonionic would cause a weakening of the chemical association between the chemical linker and the organic chemical and/or anionic surfactant.

The complex of the organic chemical and chemical linker can be applied neat to the surface which is being treated, wherein the chemical linker functions to bind the organic chemical to the treated surface. Alternatively, the complex of the organic chemical and the chemical linker can be dissolved at a concentration of about 0.1 wt. % to about 99.9 wt. % in a solvent which dissolves both the chemical linker and organic chemical. Alternatively, the complex of the chemical linker and the organic chemical can be incorporated into a cleaning composition such as a body cleansing formulation, a fabric softening composition, a body lotion, a shampoo, an oral cleaning composition, a light duty liquid composition, an all purpose or microemulsion hard surface cleaning composition and a fabric care cleaning composition.

The instant invention also relates to complexes of a chemical linker, an organic chemical having a dipole moment of at least about 1.5 Debyes and an anionic sulfonate, carboxylate or sulfate containing surfactant which can be optionally mixed with a zwitterionic surfactant or an amine oxide and mixtures thereof.

DETAILED DESCRIPTION OF THE INVENTION

The present invention relates to a complex of:

(a) an organic chemical having a chemical group having a dipole moment of at least about 1.5 Debyes, more preferably at least about 1.6 Debyes; and (b) a chemical linker selected from the group consisting of carboxylic acids having 4 to 6 carbon atoms, polyethylene glycols having a molecular weight of about 600 to about 10,000, an ethoxylated polyhydric alcohol and a polyvinyl pyrrolidone, polymer wherein the mole ratio of the organic chemical to chemical linker is about 4:1 to about 1:4. The present invention also relates to a solution of 0.25 wt. % to 99.75 wt. % of the complex of the organic chemical and chemical linker in a solvent which can solubilize the complex of the organic chemical and chemical linker, wherein the composition does not contain an N-alkyl aldonamide, an alkylene carbonate, a nonionic water-soluble cellulose polymer, a $C_8$–$C_{18}$ alkylamide $C_2$–$C_3$ alkyl di $C_1$–$C_2$ alkylamine, cyclomethicone, a linear anionic polycarboxylate such as a copolymer of vinyl methyl ether and maleic anhydride, and a mono, di or triester of an ethoxylated polyhydric alcohol having the formula:

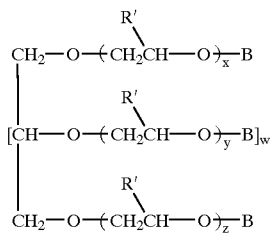

Formula (I)

wherein w equals one to four B is selected from the group consisting of hydrogen and a group represented by:

wherein R is selected from the group consisting of alkyl group having about 6 to 22 carbon atoms, and alkenyl groups having about 6 to 22 carbon atoms, wherein at least one of the B group is represented by said

and R' is selected from the group consisting of hydrogen and methyl groups; x, y and z have a value between 0 to 60, provided that (x+y+z) equals about 2 to about 100, wherein in Formula (I) the ratio of monoester/diester/triester is 45 to 90/5 to 40/1 to 20.

The present invention further relates to a composition which comprises:

(a) 0.1 to 10 wt. % of an organic chemical having a chemical group with dipole moment of at least about 1.5 Debyes, more preferably at least about 1.6 Debyes;

(b) 0 to 30 wt. % of at least one anionic surfactant having a carboxylate, sulfate or sulfonate group;

(c) 0.1 to 20 wt. % of a chemical linker compound selected from the group consisting of an ethoxylated polyhydric alcohol, a polyvinyl pyrrolidone polymer, a polyethylene glycol having a molecular weight of about 600 to 10,000 and a carboxylic acid having 4 to 6 carbon atoms and mixtures thereof, wherein the chemical linker complexes both with the anionic surfactant and the additive;

(d) 0 to 15 wt. % of a second surfactant selected from the group consisting of an amine oxide surfactant and a zwitterionic surfactant and mixtures thereof, wherein the anionic surfactant complexes with the amine oxide or zwitterionic surfactant;

(e) 0 to 20 wt. % of a cosurfactant; and (f) 50 to 99.8 wt. % of water, wherein the composition does not contain an N-alkyl aldonamide, alkylene carbonate, a nonionic water-soluble cellulose polymer, a $C_8$–$C_{18}$ alkylamide $C_2$–$C_3$ alkyl di $C_1$–$C_2$ alkylamine, cyclomethicone, a linear anionic polycarboxylate such as a copolymer of vinyl methyl ether and maleic anhydride, and a mono, di or triester of an ethoxylated polyhydric alcohol having the formula:

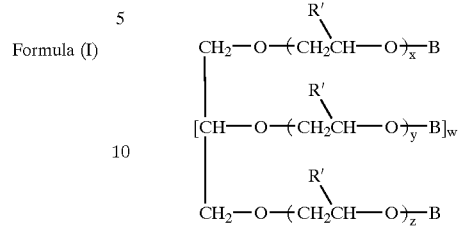

Formula (I)

wherein w equals one to four B is selected from the group consisting of hydrogen and a group represented by:

wherein R is selected from the group consisting of alkyl group having about 6 to 22 carbon atoms, and alkenyl groups having about 6 to 22 carbon atoms, wherein at least one of the B group is represented by said

and R' is selected from the group consisting of hydrogen and methyl groups; x, y and z have a value between 0 to 60, provided that (x+y+z) equals about 2 to about 100, wherein in Formula (I) the ratio of monoester/diester/triester is 45 to 90/5 to 40/1 to 20.

The compositions of the instant invention can be in the form of a solution, a microemulsion, a gel or a paste.

The complex of the organic chemical and chemical linker can be made by simple mixing with or without heat, if the chemical linker is a liquid. If the chemical linker is a solid, the chemical linker must be heat above its melting point and the organic chemical mixed into the melted chemical linker.

The organic chemicals used in the instant invention have chemical group having dipole moments of at least about 1.5 Debyes, more preferably at least one about 1.6 Debyes such as halogens affixed to a carbon atom, alcohol groups, aldehyde groups, ester groups, carboxylic acid groups, amine groups and amide groups. Typical chemical additives containing groups with high dipole moments are perfumes containing alcohol and aldehyde compounds, an insect repellent such as an N-lower alkyl neoalkanoamide wherein the alkyl group has 1 to 4 carbon atoms and the neodalkanoyl moiety has 7 to 14 carbon atoms, antibacterial agents such as triclosan, (2,4,4'-trichloro-2-hydroxy diphenyl ether, essential oils, 3,4,4'-trichlorocarbanilide, benzoic esters and parachloro metal xylenol and mixtures thereof, enzymes, proteins and allergen such as benzyl benzoate.

As used herein and in the appended claims one of the organic chemicals is a perfume which is used in its ordinary sense to refer to and include any non-water soluble fragrant substance or mixture of substances including natural (i.e., obtained by extraction of flower, herb, blossom or plant), artificial (i.e., mixture of natural oils or oil constituents) and synthetically produced substance) odoriferous substances. Typically, perfumes are complex mixtures of blends of various organic compounds such as alcohols, aldehydes, ethers, aromatic compounds and varying amounts of essential oils (e.g., terpenes) such as from 0% to 80%, usually from 10% to 70% by weight. The essential oils themselves are volatile odoriferous compounds and also serve to dissolve the other components of the perfume.

The analephotropic negatively charged anionic complex which can be contained in the instant cleaning compositions such as a fabric cleaning composition, a light duty liquid composition, an all purpose or microemulsion composition, a body cleaning composition or a shampoo comprises a complex of:

(a) at least one anionic surfactant which is an alkali metal salt or an alkaline earth metal salt of a sulfonate or sulfate surfactant; and (b) an amine oxide or zwitterionic surfactant wherein the ratio of the anionic surfactant to the amine oxide surfactant, zwitterionic surfactant is 7:1 to 0.2:1, more preferably 2:1 to 0.4:1. The instant composition contains about 3 to about 40 wt. %, more preferably about 5 to about 20 wt. % of the analephotropic negatively charged complex.

Suitable water-soluble non-soap, anionic surfactants include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble detergent. Usually, the hydrophobic group will include or comprise a $C_8$–$C_{22}$ alkyl, alkyl or acyl group. Such surfactants are employed in the form of water-soluble salts and the salt-forming cation usually is selected from the group consisting of sodium, potassium, or magnesium, with the sodium and magnesium cations again being preferred.

Examples of suitable sulfonated anionic surfactants are the well known higher alkyl mononuclear aromatic sulfonates such as the higher alkyl benzene sulfonates containing from 10 to 16 carbon atoms in the higher alkyl group in a straight or branched chain, $C_8$–$C_{15}$ alkyl toluene sulfonates and $C_8$–$C_{15}$ alkyl phenol sulfonates.

A preferred sulfonate is linear alkyl benzene sulfonate having a high content of 3-(or higher) phenyl isomers and a correspondingly low content (well below 50%) of 2-(or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low. Particularly preferred materials are set forth in U.S. Pat. No. 3,320,174.

Other suitable anionic surfactants are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, preferably 12 to 21 carbon atoms and having the formula $RCH=CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred olefin sulfonates contain from 14 to 16 carbon atoms in the R alkyl group and are obtained by sulfonating an a-olefin.

Other examples of suitable anionic sulfonate surfactants are the paraffin sulfonates containing 10 to 20, preferably 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos. 2,503,280; 2,507,088; 3,260,744; 3,372,188; and German Patent 735,096.

Examples of satisfactory anionic sulfate surfactants are the $C_8$–$C_{18}$ alkyl sulfate salts and the ethoxylated $C_8$–$C_{18}$ alkyl sulfate salts and the ethoxylated $C_8$–$C_{18}$ alkyl ether sulfate salts having the formula $R(OC_2H_4)_n$ $OSO_3M$ wherein n is 1 to 12, preferably 1 to 5, and M is a metal cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product.

On the other hand, the ethoxylated alkyl ether sulfates are obtained by sulfating the condensation product of ethylene oxide with a $C_8$–$C_{18}$ alkanol and neutralizing the resultant product. The alkyl sulfates may be obtained by sulfating the alcohols obtained by reducing glycerides of coconut oil or tallow or mixtures thereof and neutralizing the resultant product. The ethoxylated alkyl ether sulfates differ from one another in the number of moles of ethylene oxide reacted with one mole of alkanol. Preferred alkyl sulfates and preferred ethoxylated alkyl ether sulfates contain 10 to 16 carbon atoms in the alkyl group.

The ethoxylated $C_8$–$C_{12}$ alkylphenyl ether sulfates containing from 2 to 6 moles of ethylene oxide in the molecule also are suitable for use in the inventive compositions. These surfactants can be prepared by reacting an alkyl phenol with 2 to 6 moles of ethylene oxide and sulfating and neutralizing the resultant ethoxylated alkylphenol.

Other suitable anionic surfactants are the $C_9$–$C_{15}$ alkyl ether polyethenoxyl carboxylates having the structural formula $R(OC_2H_4)_nOX$ COOH wherein n is a number from 4 to 12, preferably 5 to 10 and X is selected from the group consisting of

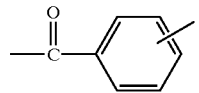

wherein $R_1$ is a $C_1$–$C_3$ alkylene group. Preferred compounds include $C_9$–$C_{11}$ alkyl ether polyethenoxy (7–9) C(O) $CH_2CH_2COOH$, $C_{13}$–$C_{15}$ alkyl ether polyethenoxy (7–9)

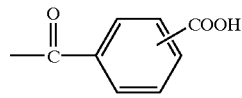

and $C_{10}$–$C_{12}$ alkyl ether polyethenoxy (5–7) $CH_2COOH$. These compounds may be prepared by considering ethylene oxide with appropriate alkanol and reacting this reaction product with chloracetic acid to make the ether carboxylic acids as shown in U.S. Pat. No. 3,741,911 or with succinic anhydride or phthalic anhydride. Obviously, these anionic surfactants will be present either in acid form or salt form depending upon the pH of the final composition, with salt forming cation being the same as for the other anionic surfactants.

Of the foregoing non-soap anionic surfactants used in forming the analephotropic complex, the preferred surfactants are the sodium or magnesium salts of the $C_8$–$C_{18}$ alkyl sulfates such as magnesium lauryl sulfate and sodium lauryl sulfate and mixtures thereof.

Generally, the proportion of the nonsoap-anionic surfactant will be in the range of 0 to 30%, preferably from 1% to 15%, by weight of the cleaning composition.

The instant composition contains as part of the analephotropic negatively charged complex about 3% to about 30%, preferably about 4% to about 15% of an amine oxide, alkylene carbonate or zwitterionic surfactant.

The amine oxides used in forming the analephotropic complex are depicted by the formula

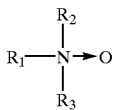

wherein $R_1$ is a $C_{10}$–$C_{18}$ a linear or branched chain alkyl group, $R_2$ is a $C_1$–$C_{16}$ linear alkyl group and $R_3$ is a $C_1$–$C_{16}$ linear alkyl group.

The zwitterionic surfactant used in forming the analephotropic complex is a water soluble betaine having the general formula:

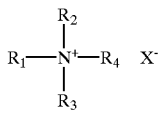

wherein $X^-$ is selected from the group consisting of $COO^-$ and $SO_3^-$ and $R_1$ is an alkyl group having 10 to about 20 carbon atoms, preferably 12 to 16 carbon atoms, or the amido radical:

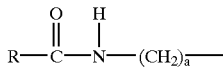

wherein R is an alkyl group having about 9 to 19 carbon atoms and a is the integer 1 to 4: $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N, N-dimethyl-ammonia) acetate, coco dimethyl betaine or 2-(N-coco N, N-dimethylammonia) acetate, myristyl dimethyl betaine, palmityl dimethyl betaine, lauryl dimethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine. Three preferred betaine surfactants are Genagen CAB and Rewoteric AMB 13 and Golmschmidt Betaine L7.

The instant compositions contain about 0.5 wt. % to about 10 wt. %, more preferably about 1 wt. % to about 7.0 wt. % of a chemical linker which can be a carboxylic acid having 4 to 6 carbon atoms, a Lewis base, neutral polymer which is soluble in water and has either a nitrogen or oxygen atom with a pair of free electrons such that the Lewis base, neutral polymer can electronically associate with the anionic surfactant and an active organic chemical having a dipole moment of at least about 1.5 Debyes such as an enzyme, protein, allergen agent, a perfume or an antimicrobial agent such as triclosan or an insect repellent such as MNDA wherein the Lewis base, neutral polymer is deposit and anchors onto the surface of the surface being treated thereby holding the organic chemical in close proximity to the surface thereby ensuring that the properties being parted by the organic chemical last longer. The chemical linker can also link with the anionic surfactant to hold the anionic surfactant in close proximity to the surface being cleaned.

The Lewis base, neutral polymers are selected from the group consisting of an ethoxylated polyhydric alcohol, a polyvinyl pyrrolidone polymer and a polyethylene glycol.

The ethoxylated polyhydric alcohol is depicted by the following formula:

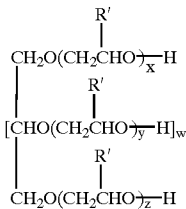

wherein w equals one to four and x, y and z have a value between 0 and 60, more preferably 0 to 40, provided that (x+y+z) equals about 2 to about 100, preferably about 4 to about 24 and most preferably about 4 to about 19, and wherein R' is either hydrogen atom or methyl group. A preferred ethoxylated polyhydric alcohol is glycerol 6EO.

The polyvinyl pyrrolidone polymer is depicted by the formula:

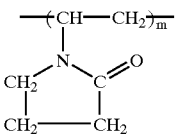

wherein m is about 20 to about 350 more preferably about 70 to about 110.

The polyethylene glycol is depicted by the formula

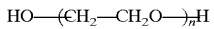

wherein n is about 8 to about 225, more preferably about 10 to about 100,000, wherein PEG1000 is preferred which is a polyethylene glycol having a molecular weight of about 1000.

A cosurfactant can be optionally used in forming the cleaning compositions of the instant invention. Suitable cosurfactants over temperature ranges extending from 4° C. to 43° C. are: (1) water-soluble $C_3$–$C_4$ alkanols, polypropylene glycol of the formula $HO(CH_3CHCH_2O)_nH$ wherein n is a number from 2 to 18 and copolymers of ethylene oxide and propylene oxide and mono $C_1$–$C_6$ alkyl ethers and esters of ethylene glycol and propylene glycol having the structural formulas $R(X)_nOH$ and $R_1(X)_nOH$ wherein R is $C_1$–$C_6$ alkyl, $R_1$ is $C_2$–$C_4$ acyl group, X is ($OCH_2CH_2$) or ($OCH_2(CH_3)CH$) and n is a number from 1 to 4.

Representative members of the polypropylene glycol include dipropylene glycol and polypropylene glycol having a molecular weight of 200 to 1000, e.g., polypropylene glycol 400. Other satisfactory glycol ethers are ethylene glycol monobutyl ether (butyl cellosolve), diethylene glycol monobutyl ether (butyl carbitol), triethylene glycol monobutyl ether, mono, di, tri propylene glycol monobutyl ether, tetraethylene glycol monobutyl ether, mono, di, tripropylene glycol monomethyl ether, propylene glycol monomethyl ether, ethylene glycol monohexyl ether, diethylene glycol monohexyl ether, propylene glycol tertiary butyl ether, ethylene glycol monoethyl ether, ethylene glycol monomethyl ether, ethylene glycol monopropyl ether, ethylene glycol monopentyl ether, diethylene glycol monomethyl ether, diethylene glycol monoethyl ether, diethylene glycol monopropyl ether, diethylene glycol monopentyl ether, triethylene glycol monomethyl ether, triethylene glycol monoethyl ether, triethylene glycol monopropyl ether, triethylene glycol monopentyl ether, triethylene glycol monohexyl ether, mono, di, tripropylene glycol monoethyl ether, mono, di tripropylene glycol monopropyl ether, mono, di, tripropylene glycol monopentyl ether, mono, di, tripropylene glycol monohexyl ether, mono, di, tributylene glycol mono methyl ether, mono, di, tributylene glycol monoethyl ether, mono, di, tributylene glycol monopropyl ether, mono, di, tributylene glycol monobutyl ether, mono, di, tributylene glycol monopentyl ether and mono, di, tributylene glycol monohexyl ether, ethylene glycol monoacetate and dipropylene glycol propionate. Representative members of the aliphatic carboxylic acids include $C_3$–$C_6$ alkyl and alkenyl monobasic acids such as acrylic acid and propionic acid and dibasic acids such as glutaric acid and mixtures of glutaric acid with adipic acid and succinic acid, as well as mixtures of the foregoing acids.

While all of the aforementioned glycol ether compounds and acid compounds provide the described stability, the most preferred cosurfactant compounds of each type, on the basis of cost and cosmetic appearance (particularly odor), are diethylene glycol monobutyl ether and a mixture of adipic, glutaric and succinic acids, respectively. The ratio of acids in the foregoing mixture is not particularly critical and can be modified to provide the desired odor. Generally, to maximize water solubility of the acid mixture glutaric acid, the most water-soluble of these three saturated aliphatic dibasic acids, will be used as the major component.

Still other classes of cosurfactant compounds providing stable cleaning compositions at low and elevated temperatures are the mono-, di- and triethyl esters of phosphoric acid such as triethyl phosphate.

The amount of cosurfactant which might be required to stabilize the cleaning compositions will, of course, depend on such factors as the surface tension characteristics of the cosurfactant, the type and amounts of the analephotropic complex and perfumes, and the type and amounts of any other additional ingredients which may be present in the composition and which have an influence on the thermodynamic factors enumerated above. Generally, amounts of cosurfactant in the range of from 0 to 50 wt. %, preferably from 0.1 wt. % to 25 wt. %, especially preferably from 0.5 wt. % to 15 wt. %, by weight provide stable microemulsions for the above-described levels of primary surfactants and perfume and any other additional ingredients as described below.

The present invention also relates to a stable concentrated microemulsion or acidic microemulsion composition comprising approximately by weight:

(a) 0 to 30%, more preferably 1% to 15% of at least one anionic surfactant containing carboxylate, sulfonate or sulfate groups;

(b) 0 to 30%, more preferably 4% to 15% of a second surfactant selected from the group consisting of amine oxides and zwitterionic surfactants and mixtures thereof;

(c) 2 to 30% of a cosurfactant;

(d) 0.4% to 10% of a water insoluble perfume, antibacterial agent, allergen agent and/or an insect repellent containing amide linkages;

(e) 0 to 18% of at least one dicarboxylic acid;

(f) 0 to 1% of phosphoric acid;

(g) 0 to 0.2% of an aminoalkylene phosphoric acid;

(h) 0 to 15% of magnesium sulfate heptahydrate;

(i) 0.1% to 10% of a Lewis base, neutral polymer being complexed with the perfume, antibacterial agent and/or insect repellent containing amide linkages; and (j) the balance being water wherein the composition does not contain an N-alkyl aldonamide, a nonionic water-soluble cellulose polymer, a $C_8$–$C_{18}$ alkylamide $C_2$–$C_3$ alkyl di $C_1$–$C_2$ alkylamine, cyclomethicone, a linear anionic polycarboxylate which is a copolymer of vinyl methyl ether and maleic anhydride, and a mono, di or triester of an ethoxylated polyhydric alcohol having the formula:

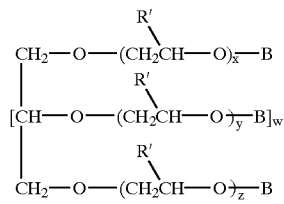

wherein w equals one to four, B is selected from the group consisting of hydrogen and a group represented by:

wherein R is selected from the group consisting of alkyl group having about 6 to 22 carbon atoms, and alkenyl groups having about 6 to 22 carbon atoms, wherein at least one of the B group is represented by said

and R' is selected from the group consisting of hydrogen and methyl groups; x, y and z have a value between 0 to 60, provided that (x+y+z) equals about 2 to about 100, wherein in said Formula a ratio of monoester/diester/triester is 45 to 90/5 to 40/1 to 20.

The present invention also relates to a light duty liquid composition or light duty liquid microemulsion composition which comprises approximately by weight:

(a) 0 to 30%, more preferably 1% to 15% of an anionic surfactant containing carboxylate, sulfate or sulfonate;

(b) 0 to 30%, more preferably 4% to 15% of a second surfactant selected from the group consisting of amine oxides and zwitterionic surfactants and mixtures thereof;

(c) 0 to 10% of a perfume, allergen agent and/or antibacterial agent;

(d) 0 to 25% of a cosurfactant;

(e) 0.1% to 10% of a Lewis base, neutral polymer being complexed with said perfume, allergen agent and/or antibacterial; and (f) the balance being water wherein the composition does not contain an N-alkyl aldonamide, a nonionic water-soluble cellulose polymer, a $C_8$–$C_{18}$ alkylamide $C_2$–$C_3$ alkyl di $C_1$–$C_2$ alkylamine, cyclomethicone, a linear anionic polycarboxylate which is a copolymer of vinyl methyl ether and maleic anhydride, and a mono, di or triester of an ethoxylated polyhydric alcohol having the formula:

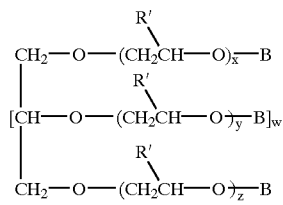

wherein w equals one to four, B is selected from the group consisting of hydrogen and a group represented by:

wherein R is selected from the group consisting of alkyl group having about 6 to 22 carbon atoms, and alkenyl groups having about 6 to 22 carbon atoms, wherein at least one of the B group is represented by said

and R' is selected from the group consisting of hydrogen and methyl groups; x, y and z have a value between 0 to 60, provided that (x+y+z) equals about 2 to about 100, wherein in said Formula a ratio of monoester/diester/triester is 45 to 90/5 to 40/1 to 20.

A typical shampoo formula utilizing linker chemicals comprises approximately by weight:

(a) 10% to 30% of an ammonium or alkali metal salt of an ethoxylated $C_8$–$C_{16}$ alkyl ether sulfate, a $C_8$–$C_{16}$ alkyl benzene sulfonate or a $C_8$–$C_{16}$ alkyl sulfate;
(b) 0.1% to 4% of a dimethyl polysiloxane;
(c) 0 to 3% of a $C_{12-16}$ alkyl diethanol amide;
(d) 0.1% to 3% of a $C_{20}$–$C_{40}$ alcohol;
(e) 0 to 1.5% of a distearyldimonium chloride;
(f) 0.1% to 2.0% of perfume;
(g) 0.1% to 6% of a chemical linker;
(h) 0 to 4% of a zwitterionic surfactant which is complexed with said anionic surfactant; and
(i) the balance being water.

A typical body cleaning composition comprises approximately by weight:

(a) 6% to 30% of an ethoxylated $C_8$–$C_{16}$ alkyl ether sulfate;
(b) 2% to 16% of a $C_8$–$C_{16}$ alkyl sulfate or a $C_8$–$C_{16}$ alkyl benzene sulfonate;
(c) 1% to 8% of a zwitterionic surfactant being complexed with said sulfate and said sulfonate surfactant;
(d) 1% to 8% of a $C_{12-16}$ alkyl diethanol amide;
(e) 0.1% to 5% of an organic chemical selected from the group consisting of perfume, protein and an antibacterial agent and mixtures thereof;
(f) 0.5% to 6% of a chemical linker selected from the group consisting of carboxylic acids having 4 to 6 carbon atoms, an ethoxylated polyhydric alcohol, a polyvinyl pyrrolidone polymer and a polyethylene glycol having a molecular weight of about 600 to about 10,000, wherein the molar ratio of the chemical linker to the organic chemical is about 4:1 to 1:4; and
(h) the balance being water wherein the composition does not contain an N-alkyl aldonamide, a nonionic water-soluble cellulose polymer, a $C_8$–$C_{18}$ alkylamide $C_2$–$C_3$ alkyl di $C_1$–$C_2$ alkylamine, cyclomethicone, a linear anionic polycarboxylate which is a copolymer of vinyl methyl ether and maleic anhydride, and a mono, di or triester of an ethoxylated polyhydric alcohol having the formula:

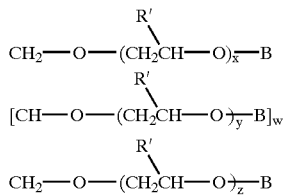

wherein w equals one to four, B is selected from the group consisting of hydrogen and a group represented by:

wherein R is selected from the group consisting of alkyl group having about 6 to 22 carbon atoms, and alkenyl groups having about 6 to 22 carbon atoms, wherein at least one of the B group is represented by said

and R' is selected from the group consisting of hydrogen and methyl groups; x, y and z have a value between 0 to 60, provided that (x+y+z) equals about 2 to about 100, wherein in said Formula a ratio of monoester/diester/triester is 45 to 90/5 to 40/1 to 20.

A typical fabric care cleaning composition comprises approximately by weight:

(a) 5% to 40% of a sulfate or sulfonate surfactant;
(b) 0.1% to 5% of a chemical linker;
(c) 0.05% to 5% of at least one enzyme; and
(d) the balance being water.

In addition to the above-described essential ingredients required for the formation of the cleaning compositions, the compositions of this invention may often and preferably do contain one or more additional ingredients which serve to improve overall product performance.

One such ingredient is an inorganic or organic salt of oxide of a multivalent metal cation, particularly $Mg^{++}$. The metal salt or oxide provides several benefits including improved cleaning performance in dilute usage, particularly in soft water areas, and minimized amounts of perfume required to obtain the microemulsion state. Magnesium sulfate, either anhydrous or hydrated (e.g., heptahydrate), is especially preferred as the magnesium salt. Good results also have been obtained with magnesium oxide, magnesium chloride, magnesium acetate, magnesium propionate and magnesium hydroxide. These magnesium salts can be used with formulations at neutral or acidic pH since magnesium hydroxide will not precipitate at these pH levels.

Although magnesium is the preferred multivalent metal from which the salts (inclusive of the oxide and hydroxide) are formed, other polyvalent metal ions also can be used provided that their salts are nontoxic and are soluble in the aqueous phase of the system at the desired pH level.

Thus, depending on such factors as the pH of the system, the nature of the analephotropic complex or anionic surfactant and cosurfactant, as well as the availability and cost factors, other suitable polyvalent metal ions include aluminum, copper, nickel, iron, calcium, etc. It should be noted, for example, that with the preferred paraffin sulfonate anionic detergent calcium salts will precipitate and should not be used. It has also been found that the aluminum salts work best at pH below 5 or when a low level, for example 1 weight percent, of citric acid is added to the composition which is designed to have a neutral pH. Alternatively, the aluminum salt can be directly added as the citrate in such case. As the salt, the same general classes of anions as mentioned for the magnesium salts can be used, such as halide (e.g., bromide, chloride), sulfate, nitrate, hydroxide, oxide, acetate, propionate, etc.

The cleaning compositions can optionally include from 0 to 2.5 wt. %, preferably from 0.1 wt. % to 2.0 wt. % of the composition of a $C_8$–$C_{22}$ fatty acid or fatty acid soap as a foam suppressant. The addition of fatty acid or fatty acid soap provides an improvement in the rinseability of the composition whether applied in neat or diluted form. Generally, however, it is necessary to increase the level of cosurfactant to maintain product stability when the fatty acid or soap is present. If more than 2.5 wt. % of a fatty acid is used in the instant compositions, the composition will become unstable at low temperatures as well as having an objectionable smell.

As example of the fatty acids which can be used as such or in the form of soap, mention can be made of distilled coconut oil fatty acids, "mixed vegetable" type fatty acids (e.g. high percent of saturated, mono-and/or polyunsaturated $C_{18}$ chains); oleic acid, stearic acid, palmitic acid, eiocosanoic acid, and the like, generally those fatty acids having from 8 to 22 carbon atoms being acceptable.

The liquid cleaning compositions of this invention may, if desired, also contain other components either to provide additional effect or to make the product more attractive to the consumer. The following are mentioned by way of example: Colors or dyes in amounts up to 0.5% by weight; bactericides in amounts up to 1% by weight; preservatives or antioxidizing agents, such as formalin, 5-chloro-2-methyl-4-isothaliazolin-3-one, 2,6-di-tert.butyl-p-cresol, etc., in amounts up to 2% by weight; and pH adjusting agents, such as sulfuric acid or sodium hydroxide, as needed. Furthermore, if opaque compositions are desired, up to 4% by weight of an opacifier may be added.

In final form, the cleaning compositions exhibit stability at reduced and increased temperatures. More specifically, such compositions remain clear and stable in the range of 4° C. to 50° C., especially 10° C. to 43° C. Such compositions exhibit a pH in the acid or neutral range depending on intended end use. The liquids are readily pourable and exhibit a viscosity in the range of 6 to 60 milliPascal-Second (mPas.) as measured at 25° C. with a Brookfield RVT Viscometer using a #1 spindle rotating at 20 RPM. Preferably, the viscosity is maintained in the range of 10 to 40 mPas.

The compositions are directly ready for use or can be diluted as desired and in either case no or only minimal rinsing is required and substantially no residue or streaks are left behind. When intended for use in the neat form, the liquid compositions can be packaged under pressure in an aerosol container or in a pump-type sprayer for the so-called spray-and-wipe type of application.

Because the compositions as prepared are aqueous liquid formulations and since no particular mixing is required to form the all purpose cleaning or microemulsion composition, the compositions are easily prepared simply by combining all the ingredients in a suitable vessel or container. The order of mixing the ingredients is not particularly important and generally the various ingredients can be added sequentially or all at once or in the form of aqueous solutions of each or all of the primary detergents and cosurfactants can be separately prepared and combined with each other and with the perfume. The magnesium salt, or other multivalent metal compound, when present, can be added as an aqueous solution thereof or can be added directly. It is not necessary to use elevated temperatures in the formation step and room temperature is sufficient.

The following examples illustrate the complexes of additives and chemical linker and liquid cleaning compositions containing complexes of the chemical linker with the additive and/or surfactant invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE I

The following complexes of chemical additive and chemical linker were made:

Tests were run with a microcalorimeter CALVET. A cell contains 0.5 g of the chemical additive and 0.5 g of a chemical linker such as polyethylene glycol in two separated parts. A semi circular cup disposed with in the cell allows the mixing of the two components in the cell. The heat flow generated by the mixing is measured. If the components interact together, their mixing releases heat. The table hereafter gives the components of the mixture, the time and the microwatt value to the maximum of the exothermic peak.

| Chemical additives | A | B | C | D | E | F | G | H | I | J |
|---|---|---|---|---|---|---|---|---|---|---|
| Quat ester | 0.5 | | | | | | | | | |
| Benzyl benzoate | | 0.5 | | | | | | | | |
| Dihydromyrcenol - Perfume | | | 0.5 | | | | | | | |
| Aldehyde C9 - Perfume | | | | 0.5 | | | | | 0.5 | |
| Triclosan | | | | | 0.5 | | | | | |
| MNDA | | | | | | | 0.5 | | | 1.5 |
| n-dimethyl para-amine octyl benzoate | | | | | | | | 0.5 | | |
| BSA - Protein | | | | | | | | | 0.5 | |
| PEG 200 | | | | 0.5 | | | | | | |
| PEG 600 | 0.5 | 0.5 | | | 0.5 | | | 0.5 | | |

-continued

| Chemical additives | A | B | C | D | E | F | G | H | I | J |
|---|---|---|---|---|---|---|---|---|---|---|
| PEG 6000 | | | 0.5 | | | 0.5 | 0.5 | | | |
| Exothermic reaction | | | | | | | | | | |
| Microwatte to exothermic energy peak | 1070 | 3240 | 115 | 55500 | 327 | 171 | 98 | 700 | 39700 | 1934 |
| Time (seconds) to energy peak | 80 | 130 | 30 | 40 | 120 | 130 | 140 | 820 | 380 | 670 |
| Levenol F-200 | | | | | | | | | 0.5 | |
| Isobutyric Acid | | | | | | | | | | 0.3 |

EXAMPLE II

The following formulas were made by simple mixing at 25° C. and tested for roach repelling.

| | Weight Percent | | | | |
|---|---|---|---|---|---|
| | A | B | C | D | E |
| Deionized Water | 82.2260 | 83.2260 | 82.9260 | 84.9260 | 83.9260 |
| MgSO4·7H2O | 1.0000 | 1.0000 | 1.0000 | 1.0000 | 1.0000 |
| $C_{14-17}$ Paraffin Sulfonate 60% No P | 6.6700 | 6.6700 | 6.6700 | 6.6700 | 6.6700 |
| $C_{13-15}$ Fatty Alcohol EO 7:1/PO 4:1 | 3.0000 | 3.0000 | 0.0000 | 0.0000 | 0.0000 |
| Esterified Polyethoxyether Levenol F200 | 0.0000 | 0.0000 | 2.3000 | 2.3000 | 2.3000 |
| PEG-600 | 0.0000 | 1.0000 | 0.0000 | 0.0000 | 1.0000 |
| Diethylene Glycol Monobutyl Ether | 3.5000 | 2.5000 | 3.5000 | 2.5000 | 2.5000 |
| Sodium Hydroxide (38% Na2O) | 0.0500 | 0.0500 | 0.0500 | 0.0500 | 0.0500 |
| Dist. Coco Fatty Acid | 0.5000 | 0.5000 | 0.5000 | 0.5000 | 0.5000 |
| Stabilisant B 30% | 0.1540 | 0.1540 | 0.1540 | 0.1540 | 0.1540 |
| FD&C Green 3 Cl42053 | 0.0700 | 0.0700 | 0.0700 | 0.0700 | 0.0700 |
| FD&C Yellow 10 Cl 47005 | 0.0300 | 0.0300 | 0.0300 | 0.0300 | 0.0300 |
| Repellent Perfume - Mizqui | 0.8000 | 0.8000 | 0.8000 | 0.8000 | 0.8000 |
| Methyl Neodecanamide | 2.0000 | 1.0000 | 2.0000 | 1.0000 | 1.0000 |
| Days Roach Repellency, Probit 90% | 7.1000 | 1.7000 | 10.9000 | 8.8000 | 7.3000 |

The testing for roach repellency was done by a tile cup test procedure which was as follows:

German cockroaches (Blattella germancia) were maintained at 27° C. on a 12 hour light/12 hour dark photo period. Vinyl floors were cleaned and cut into 3×3 inch squares (58.1 cm$^2$) with an electric saw. A 1.5 cm square notch was cut out of half of the resulting squares to provide the roaches access to the shelter. The tiles were washed with water before treatment. Each of six cut tiles (two with access openings) were treated with 0.62 ml of test product (Formula L) diluted 4:1. Similarly six control tiles were treated with 0.62 ml of an identical formulation which did not contain MNDA (Formula M) diluted 4:1. The tiles were allowed to dry 4–6 hours before the cup, a six sided cube was assembled. The cut tiles were held together firmly with strips of clear tape on the outside edges, except the floor of the shelter was left unattached. The control and product treated shelter were placed in the cage and the bioassay started. Forty-eight hours prior to initiation of the assay, 50 male German cockroaches were allowed to acclimate to the pastic test cages (51×28×20 cm) with food and water available in the center, outside of the cups. A thin film of Teflon emulsion on the sides of the cages restricted the insects to the floor of the cage.

The number of insects resting on the inner walls of each cup were recorded in the middle of the photophase daily for 14 days or until equal numbers were found in treated and control cups. After counting, all roaches were removed from each cup. The position of the cups were reversed each day.

Repellency was calculated as:

$$Repellency = 100 \frac{N_t}{N_t + N_c}$$

where $N_t$ is the number of insects on the treated surface and $N_c$ is the number on the control surface. Any insect found outside of either shelter was not counted. Generally, less than 5 of the 50 insects were found outside of the shelters.

What is claimed is:

1. A stable acidic microemulsion composition comprising approximately by weight:

(a) 0 to 30% of at least one anionic surfactant containing carboxylate, sulfonate or sulfate groups;

(b) 0 to 30% of a second surfactant selected from the group consisting of amine oxides and zwitterionic surfactants and mixtures thereof;

(c) 2 to 30% of a cosurfactant;

(d) 0.4% to 10% of a water insoluble perfume, antibacterial agent, allergen agent and/or an insect repellent containing amide linkages;

(e) 0 to 18% of at least one dicarboxylic acid;

(f) 0 to 1% of phosphoric acid;

(g) 0 to 0.2% of an aminoalkylene phosphoric acid;

(h) 0 to 15% of magnesium sulfate heptahydrate;

(i) 0.1% to 10% of a Lewis base, neutral polymer being complexed with the perfume, antibacterial agent and/or insect repellent containing amide linkages, said Lewis base is selected from the group consisting of an ethoxylated polyhydric alcohol, a polyvinyl pyrrolidone and a polyethylene glycol; and (j) the balance being water, wherein the composition does not contain an N-alkyl aldonamide, a nonionic water-soluble cellulose polymer, a $C_8$–$C_{18}$ alkylamide $C_2$–$C_3$ alkyl di $C_1$–$C_2$ alkylamine, cyclomethicone, a linear anionic polycarboxylate which is a copolymer of vinyl methyl ether and maleic anhydride, and a mono, di or triester of an ethoxylated polyhydric alcohol having the formula:

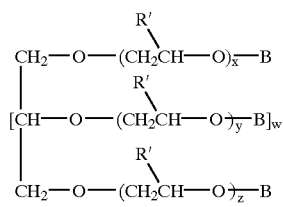

wherein w equals one to four, B is selected from the group consisting of hydrogen and a group represented by:

wherein R is selected from the group consisting of alkyl group having about 6 to 22 carbon atoms, and alkenyl groups having about 6 to 22 carbon atoms, wherein at least one of the B group is represented by said

and R' is selected from the group consisting of hydrogen and methyl groups; x, y and z have a value between 0 to 60, provided that (x+y+z) equals about 2 to about 100, wherein in said Formula a ratio of monoester/diester/triester is 45 to 90/5 to 40/1 to 20.

2. A light duty liquid composition which comprises approximately by weight:
(a) 0 to 30% of an anionic surfactant containing carboxylate, sulfate or sulfonate;
(b) 0 to 30% of a second surfactant selected from the group consisting of amine oxides and zwitterionic surfactants and mixtures thereof;
(c) 0.4% to 10% of a perfume, allergen agent and/or antibacterial agent;
(d) 0 to 25% of a cosurfactant;
(e) 0.1% to 10% of a Lewis base, neutral polymer being complexed with said perfume, allergen agent and/or antibacterial, said Lewis base is selected from the group consisting of an ethoxylated polyhydric alcohol, a polyvinyl pyrrolidone and a polyethylene glycol; and
(f) the balance being water, wherein the composition does not contain an N-alkyl aldonamide, a nonionic water-soluble cellulose polymer, a $C_8$–$C_{18}$ alkylamide $C_2$–$C_3$ alkyl di $C_1$–$C_2$ alkylamine, cyclomethicone, a linear anionic polycarboxylate which is a copolymer of vinyl methyl ether and maleic anhydride, and a mono, di or triester of an ethoxylated polyhydric alcohol having the formula:

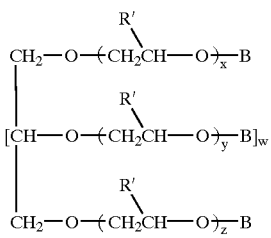

wherein w equals one to four, B is selected from the group consisting of hydrogen and a group represented by:

wherein R is selected from the group consisting of alkyl group having about 6 to 22 carbon atoms, and alkenyl groups having about 6 to 22 carbon atoms, wherein at least one of the B group is represented by said

and R' is selected from the group consisting of hydrogen and methyl groups; x, y and z have a value between 0 to 60, provided that (x+y+z) equals about 2 to about 100, wherein in said Formula a ratio of monoester/diester/triester is 45 to 90/5 to 40/1 to 20.

3. The composition of claim 2, wherein the cosurfactant is a glycol ether.

* * * * *